United States Patent
Wurzburger

[11] Patent Number: 5,949,032
[45] Date of Patent: Sep. 7, 1999

[54] STETHOSCOPE COVER AND COVERED STETHOSCOPE

[75] Inventor: Isaac Wurzburger, Monsey, N.Y.

[73] Assignee: M & W Medical Supplies LLC, Spring Valley, N.Y.

[21] Appl. No.: 09/057,242

[22] Filed: Apr. 8, 1998

[51] Int. Cl.$^6$ .................................................. A61B 7/02
[52] U.S. Cl. .............................................. 181/131; 181/137
[58] Field of Search .................................. 181/131, 137

[56] References Cited

U.S. PATENT DOCUMENTS

| | | | |
|---|---|---|---|
| 3,867,925 | 2/1975 | Ersek . | |
| 4,461,368 | 7/1984 | Plourde | 181/131 |
| 4,570,038 | 2/1986 | Tinelli | 379/452 |
| 4,867,268 | 9/1989 | Ulert | 181/137 |
| 5,424,495 | 6/1995 | Wurzberger | 181/131 |
| 5,448,025 | 9/1995 | Stark | 181/131 |
| 5,587,561 | 12/1996 | Budayr et al. | 181/131 |
| 5,686,706 | 11/1997 | Wurzburger | 181/131 |
| 5,808,244 | 9/1998 | Knight et al. | 181/131 |

*Primary Examiner*—Khanh Dang
*Attorney, Agent, or Firm*—Helfgott & Karas, PC.

[57] ABSTRACT

A stethoscope is fitted with a disposable cover to prevent cross contamination between patients. The cover is formed as a shield of material which is impermeable to liquids but which transmits sound waves. Adhesive is applied in a predetermined pattern on a portion of the cover so as to define a non adhesive fluid pathway between the central portion of the cover and its peripheral edge. This pathway adapts the cover for use with stethoscopes having vented diaphragms. Additional cover configurations are provided for use on the bell of a stethoscope.

19 Claims, 6 Drawing Sheets

STETHOSCOPE COVER AND COVERED STETHOSCOPE

BACKGROUND OF INVENTION

1. Field of the Invention

The present invention relates in general to removable sanitary covers for stethoscopes and relates in particular to a disposable cover adapted for use with a stethoscope having a vented diaphragm and also for use on the bell of a stethoscope.

2. Description of Prior Developments

Protective covers for stethoscopes are well known. Examples of such covers are shown in U.S. Pat. No. 5,686,706 which is incorporated herein by reference. A thin sheet of plastic having an adhesive backing is typically applied over the diaphragm of a stethoscope before use on each new patient. After use, the cover is typically removed and discarded.

Although these covers function adequately for most applications, a problem arises when they are used on stethoscopes having vented diaphragms. In this case, the adhesive on the inner surface of the cover seals off the vent hole and adversely affects the performance of the stethoscope. Moreover, such covers are poorly suited for use on the open rear or bell portion of a stethoscope where a tight membrane such as formed by prior covers can mask the low frequency sound waves typically transmitted through the bell.

Accordingly, a need exists for a stethoscope cover which can be applied over a vented diaphragm without adversely affecting stethoscope performance. A further need exists for such a stethoscope cover which can be applied over the open bell of a stethoscope without adversely affecting stethoscope performance.

SUMMARY OF THE INVENTION

The present invention has been developed to fulfill the needs noted above and therefore has as an object the provision of a disposable cover for a stethoscope having a vented diaphragm.

Another object of the invention is the provision of an adhesively applied stethoscope cover which avoids the plugging or obstruction of a vent hole formed in the diaphragm of a stethoscope.

Another object of the invention is the provision of a stethoscope cover adapted for use over the bell of a stethoscope.

Still another object of the invention is the provision of a sanitary disposable diaphragm cover having a fluid flow path or channel formed in its inner or adhesive side.

Yet another object of the invention is the provision of an adhesively applied disposable sanitary stethoscope cover which is available in a convenient-to-use laminated assembly.

These and other objects are met by the present invention which is directed to a thin plastic stethoscope cover having an adhesive coating which partially extends over the inner or rear surface of the cover. The pattern of adhesive is selected so that the portion of the cover located over the diaphragm vent hole lacks adhesive. In this manner, blocking or plugging of the diaphragm vent hole by the adhesive is prevented.

Numerous and varied adhesive patterns may be applied to the covers as long as the portion of the cover overlying the stethoscope vent hole is free of adhesive. It is also possible to practice the invention using a pleated cover which provides a fluid flow path between adjacent pleats and which can be deformed into a cup-shaped configuration for use on the bell of a stethoscope.

While smooth planar plastic sheets serve well as cover material for covers applied over diaphragms, somewhat cup-shaped or untensioned covers may be used over the back or bell portion of a stethoscope in accordance with another embodiment of the invention. The cup shape avoids the transmission of high frequency sound waves by preventing the cover from being tightly stretched over the bell in the manner of a diaphragm.

A stack of covers may be constructed in accordance with another embodiment of this invention wherein the adhesive backings used to secure the covers to a stethoscope are also used to hold the covers in a laminated stacked assembly. In this case, individual covers may be easily and conveniently pulled off the stack such that the need for a separate backing or cover layer over the adhesive is eliminated.

The aforementioned objects, features and advantages of the invention will, in part, be pointed out with particularity, and will, in part, become obvious from the following more detailed description of the invention, taken in conjunction with the accompanying drawings, which form an integral part thereof.

BRIEF DESCRIPTION OF THE DRAWINGS

In the drawings.

In the various figures of the drawings, like reference characters designate like parts.

DETAILED DESCRIPTION OF THE PREFERRED EMBODIMENTS

Figure 1:
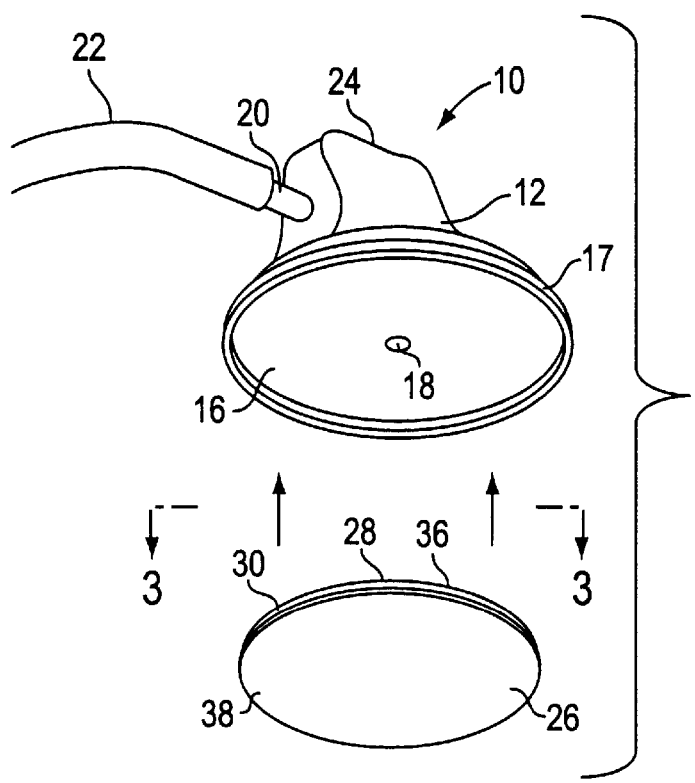
FIG. 1 is a perspective exploded view of a stethoscope head having a vented diaphragm and a stethoscope cover constructed in accordance with a first embodiment of the invention.

The present invention will now be described in conjunction with the drawings, beginning with FIG. 1 which shows a stethoscope 10 of known construction. Stethoscope 10 includes a head 12 having a diaphragm portion 14 within which a diaphragm 16 is clamped. This type of stethoscope is of the vented diaphragm type wherein a small vent hole 18 is formed in the middle of the diaphragm to allow fluid communication and pressure equalization across and through the diaphragm.

A hollow tube 20 communicates with the interior of the diaphragm portion 14 to transmit sound waves from the diaphragm through a flexible hose 22 to a user's ear. This particular stethoscope 10 does not include a cone-shaped bell portion typically provided on the back or top of the diaphragm portion 14, but rather includes a generally flat-faced solid metal ramped portion 24 of known design.

Figure 2:
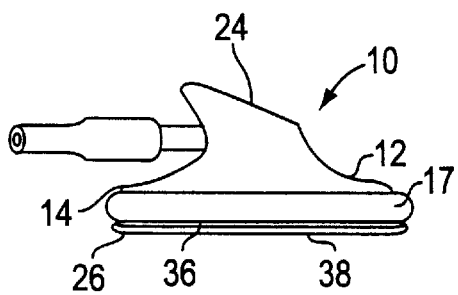
FIG. 2 is a side view of the stethoscope of FIG. 1.

As further seen in FIG. 1, a thin, circular, flexible plastic cover 26 is aligned below diaphragm 16 for attachment directly to the diaphragm as shown in FIG. 2. Cover 26 may be formed from any suitable plastic material such as cellophane, vinyl, acetate, or polyethylene.

Figure 3:
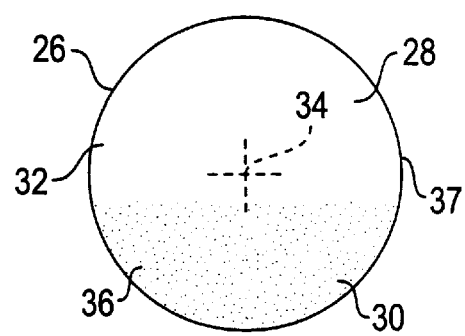
FIG. 3 is a top plan view of the stethoscope cover of FIG. 1 viewed along line 3—3 of FIG. 1.

Cover 26, as shown in FIG. 3, has an inner or attachment surface 28 divided into an adhesive portion 30 and a non adhesive portion 32. The non-adhesive portion 32 preferably extends over that portion of attachment surface 28 which directly overlies the vent hole 18 when the cover 26 is properly concentrically mounted to the diaphragm 16.

In the example shown in FIGS. 1, 2 and 3, the non-adhesive portion 32 of attachment surface 28 extends over the center 34 of the cover 26 so that when the cover is concentrically mounted over the diaphragm 16, center 34 will be substantially aligned over vent hole 18. In this manner, adhesive 36 on the adhesive portion 30 of cover 26 will not plug the diaphragm vent hole 18.

With this arrangement, as the diaphragm 16 is pressed onto a patient's skin, air from within the diaphragm portion 14 is allowed to escape through vent hole 18 as required for proper operation of the stethoscope. The air is then evacuated through a flow path formed between the non-adhesive or uncoated portion 32 and the diaphragm 16 and flows from the vent hole 18 to the peripheral edge 37 of the cover where the air escapes to the ambient atmosphere. The outer surface 38 of the cover 26 is preferably free of adhesive.

As seen in FIG. 3, the adhesive portion 30 is formed as a segment of a circle with the non-adhesive portion 32 extending over the remainder of inner surface 28, which in this embodiment includes center 34. Other adhesive patterns may be used as shown in FIGS. 4, 5, 6, 7 and 9.

Figure 4:
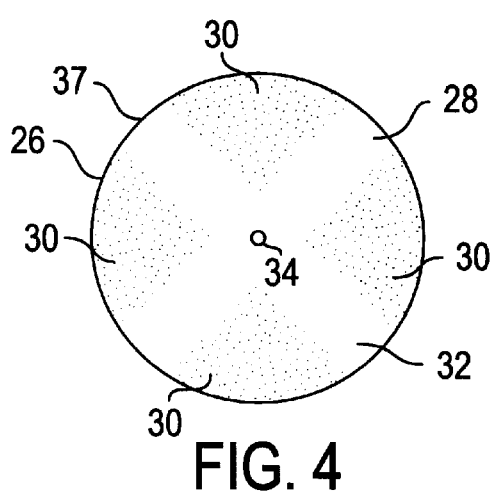
FIG. 4 is a top plan view of a stethoscope cover of the type shown in FIG. 1 having sector-shaped adhesive patterns.

In FIG. 4, inner attachment surface 28 is divided into four pie-shaped or substantially sector-shaped adhesive portions 30 which define a generally cross-shaped or X-shaped non-adhesive coated portion 32. The center 34 of cover 16 lies at the center of the non-adhesive portion 32.

Figure 5:
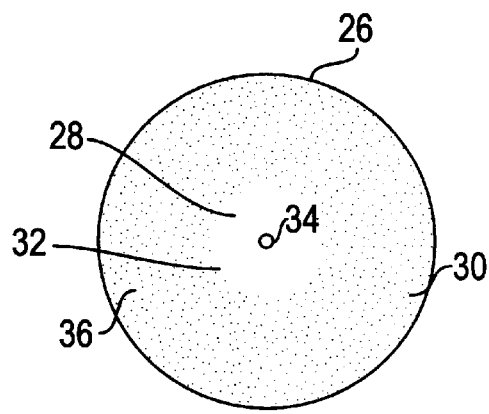
FIG. 5 is a view similar to FIG. 4 but having an annular adhesive pattern.

An annular or ring-shaped adhesive portion 30 is applied to the cover of FIG. 5 so as to define a central circular non-adhesive portion 32 concentrically arranged around center 34. In use, adhesive 36 surrounds vent hole 18 as it adheres to diaphragm 16. If the non-adhesive portion 32 is sufficiently large, the air from vent hole 18 may be received and accommodated in the circular space between the diaphragm 16 and non-adhesive portion 32 of cover 16.

Figure 6:
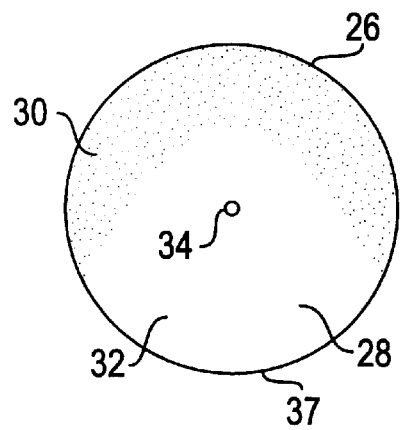
FIG. 6 is a top plan view of another cover in accordance with the invention having a crescent-shaped adhesive pattern.
Figure 7:
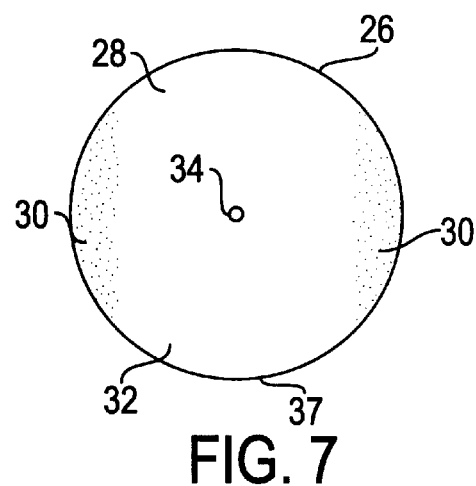
FIG. 7 is a top plan view of another embodiment of a stethoscope cover of the type shown in FIG. 1 having segment-shaped adhesive patterns formed thereon.

The cover 26 of FIG. 6 includes a crescent or arch-shaped adhesive portion 30 and a hump-shaped non-adhesive portion 28. In FIG. 7, a pair of segment-shaped adhesive portions 30 is located at diametrically opposed sides of cover 26 with non-adhesive portion 32 located there between.

Figure 8:
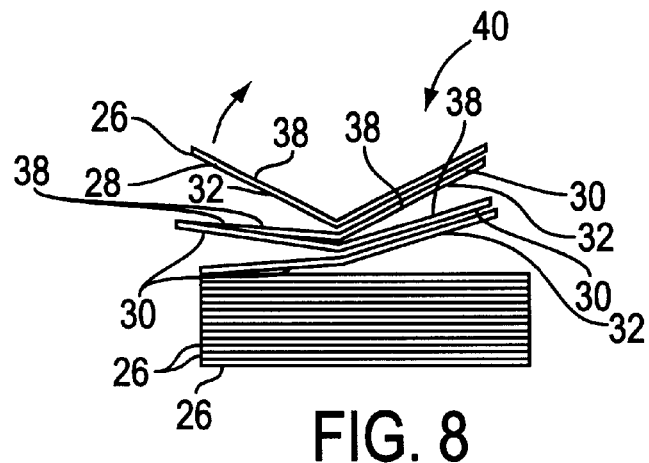
FIGS. 8 and 8A are side elevation views of a stack of a covers of the type shown in FIG. 3.

An advantage of applying adhesive over only a portion of surface 28 is that the covers 26 may be provided in the form of a self-contained dispensing stack 40 as shown in FIG. 8. That is, using a series of covers 26 such as the cover 26 shown in FIG. 3, an accordion "zig-zag" style or pleated stack can be constructed. The adhesive portion 30 of the top cover 26 is applied to the non-adhesive outer surface 38 of the next underlying cover 26. In a similar fashion, the adhesive portion 30 of the underlying or second cover is applied to the non-adhesive coated outer surface 38 of the third cover 26, and so on.

Stack 40 can be placed in a slotted box or dispenser of the type used to dispense facial tissue. In this case, after one cover is pulled through a slot in the dispenser and detached from stack 40, the next underlying cover is pulled partially through the slot for easy access and subsequent detachment from the stack.

A stack similar to stack 40 of FIG. 8 can also be constructed from a series of covers 26 having different adhesive patterns than that of FIG. 3. For example, the three sector adhesive pattern of FIGS. 9, 10, 11 and 12 can be stacked in sequential order to form a stack 40.

Figure 9:
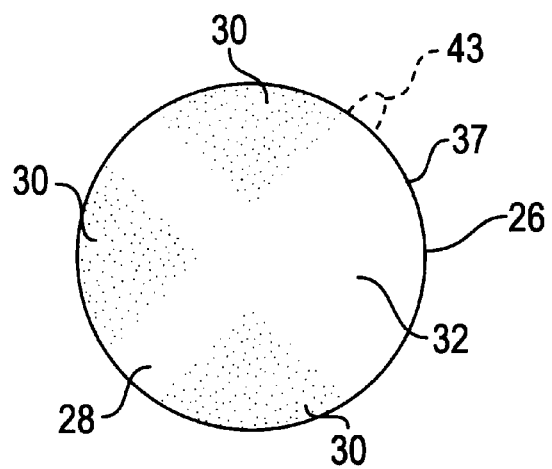
FIGS. 9 through 12 are top plan views of a cover constructed in accordance with another embodiment of the invention and having three sector-shaped adhesive patterns respectively sequentially rotated by 90 degrees for forming a stack of covers similar to that shown in FIG. 8.
Figure 10:
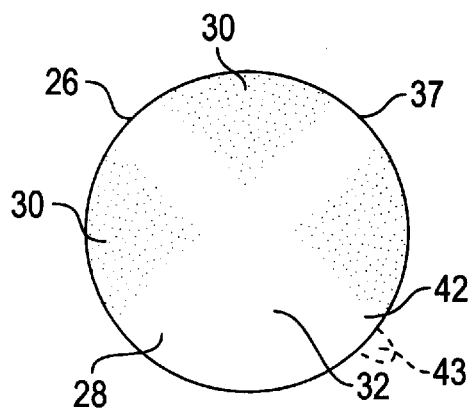

In this case, the outer surface 38 underlying the non-adhesive sector 32 at the six o'clock position of FIG. 10 is aligned over the adhesive sector 30 located at the 6 o'clock position of FIG. 9, with the non adhesive outer surface 38 of FIG. 10 applied over the adhesive or inner surface 28 of FIG. 9.

Figure 11:
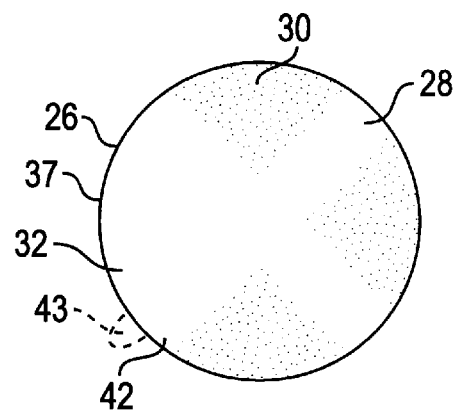
Figure 12:
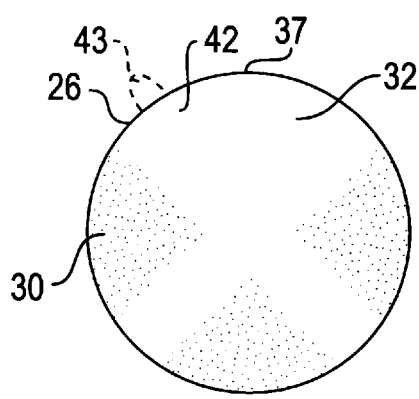

In a similar fashion, cover 26 of FIG. 11 is applied over cover 26 of FIG. 10 with the non adhesive sector 32 at the 9 o'clock position of FIG. 11 aligned over the adhesive sector portion 30 at the 9 o'clock position of FIG. 10. Cover 26 of FIG. 12 is similarly stacked on top of cover 26 of FIG. 11 with non adhesive sector 32 of FIG. 12 aligned over the 12 o'clock adhesive sector 30 of FIG. 11. This sequence is repeated to form a stack of covers similar to that shown in FIG. 8.

This somewhat spiral stacking pattern or sequential 90 degree rotation of the non-adhesive sector 32 provides a loose non-adhesive edge portion 42 which may be grasped and peeled upwardly to detach a top cover from stack 40. In this embodiment, the covers 26 are oriented such that the non adhesive outer surface 38 is exposed on top of stack 40 each time a cover 26 is removed from the stack.

Figure 8A:
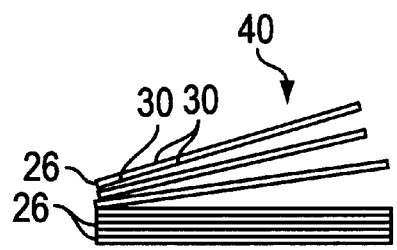

It is also possible to simply align the non adhesive sectors 32 one directly over the other in the embodiment of FIGS. 9–12 as well as in the embodiment of FIG. 3. In this case the covers can be peeled from stack 40 in the manner of adhesive edged pages from a paper notepad, that is, with the adhesive portions 30 attached to the outer surface 38 of the underlying cover 26 as shown in FIG. 8A.

Figure 13:
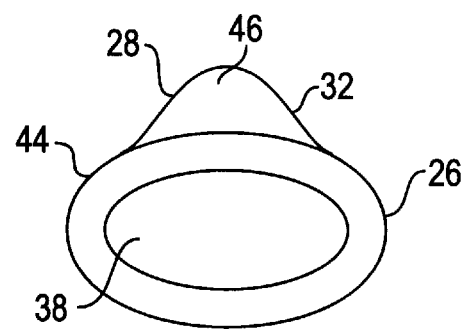
FIG. 13 is a perspective view of stethoscope cover constructed in accordance with another embodiment of the invention and particularly adapted for use on the bell portion of a stethoscope.
Figure 14:
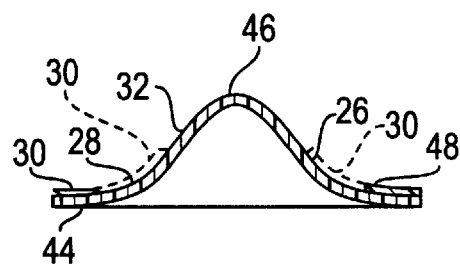
FIG. 14 is a central sectional view taken through the center of the cover of FIG. 13.

Another embodiment of the invention is shown in FIGS. 13 and 14 wherein cover 26 includes a planar annular rim 44 and a loose, flexible, collapsible central web defining a cup portion 46. The rim and web are each constructed of a homogeneous pliable plastic sheet. In this embodiment, the adhesive portion 30 is applied as an annular ring 48 encircling the cup portion 46. This embodiment is particularly adapted for use over the bell portion 52 of a stethoscope of the type shown in FIGS. 22 and 23.

Although the stethoscope diaphragm 16 is generally applied to a patient's body, in some cases, the open-ended cone-shaped bell portion of the stethoscope is placed on a patient to pick up relatively low frequency vibrations. In this case, it is desirable to avoid using a cover which is tightly sealed over the bell, insofar as such a taught cover would act as a diaphragm and transmit high frequency tones. These high frequency tones tend to obscure the lower frequency tones and adversely affect the clarity of the low frequency tone transmitted through the bell.

Accordingly, by providing adhesive on only a portion of the cover 26, the cover may be partially attached over the rim of the bell without being tensioned and thereby without interfering with the clarity of low frequency sound waves transmitted through tube 22. In use, the bell is typically held lightly against a patient's body for picking up low frequency tones. If desired, the bell can be pressed tightly against the patient's body so that the cover 26 is tightly pressed against and tensioned over the bell so as to act as a diaphragm and thereby transmit high frequency tones through the bell.

Figure 15:
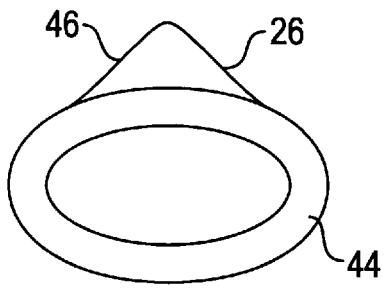
FIG. 15 is a perspective view of another embodiment of the invention.
Figure 16:
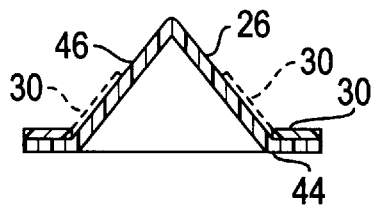
FIG. 16 is a central sectional view taken through the cover of FIG. 14.

A variation of the embodiment of FIGS. 13 and 14 is shown in FIGS. 15 and 16 wherein the central cup portion 46 is formed of a rigid or semi-rigid plastic material such that cover 26 is somewhat pliable yet retains its shape. In this embodiment the central cup portion 46 can be molded in the form of a plastic dome to match and compliment the surface contour of the recess 50 of the bell 52 of stethoscope 54 shown in FIGS. 22 and 23.

Figure 22:
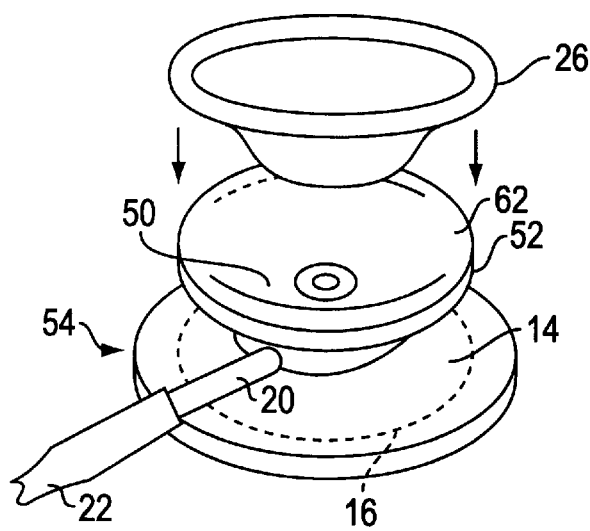
FIG. 22 is an exploded perspective view of a stethoscope cover of the type shown in either of FIGS. 13 and 14 aligned over the bell of a stethoscope head.

The collapsible cup shaped portion 46 of cover 26 of FIGS. 13 and 14 will freely shape itself to the contours of recess 50, as indicated in FIG. 22. Since the portion 46 is relatively limp, it will not transmit high frequencies and therefore is well adapted for covering the bell of the stethoscope.

Figure 17:
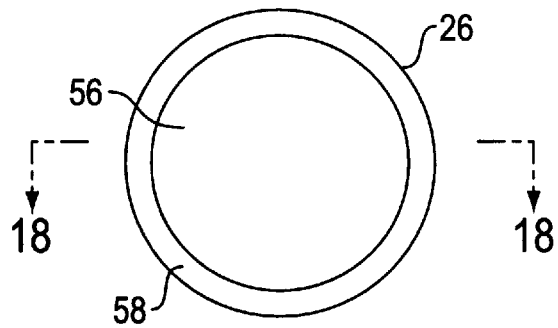
FIG. 17 is a top plan view of another embodiment of a stethoscope cover constructed in accordance with the invention.
Figure 18:
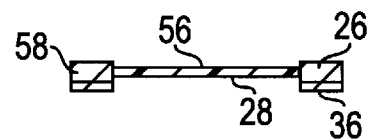
FIG. 18 is a view in section taken along line 18—18 of FIG. 17.

Another embodiment of the invention is shown in FIGS. 17 and 18 wherein a plastic cover 26 is formed with a thin central circular membrane 56 and a thicker and stiffer annular rim 58. A ring-shaped layer of adhesive 36 is applied on rim 58 for attachment to either a diaphragm or to a bell of a stethoscope. The membrane 56 is recessed within the rim 58.

Figure 19:
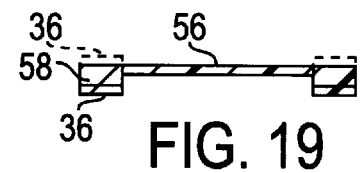
FIG. 19 is a view in section depicting a variation of the cover of FIGS. 17 and 18.

A variation of the cover 26 of FIGS. 17 and 18 shown in FIG. 19 wherein membrane 56 is coplanar with one side of rim 58 and recessed with respect to the other. In FIG. 19, adhesive 36 is shown applied to either side of rim 58, with adhesive 36 shown in dashed lines in one embodiment and solid lines in another.

Figure 20:
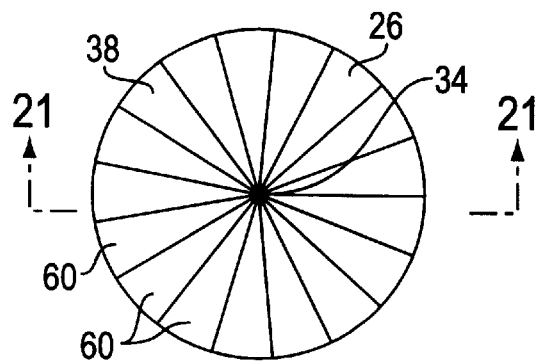
FIG. 20 is a top plan view of a pleated stethoscope cover constructed in accordance with another embodiment of the invention.
Figure 21:
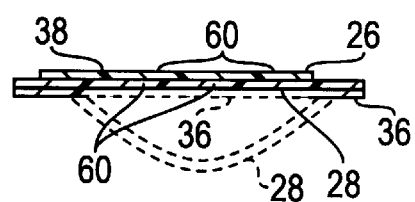
FIG. 21 is a view in section taken through line 21—21 of FIG. 19.

A pleated and layered version of a stethoscope cover 26 is shown in FIGS. 20 and 21. A thin sheet of cellophane or similar plastic material is folded into a circular array of sector shaped pleats 60. As seen in FIG. 21, pleats 60 partially overlap one another in the manner of a folding fan. The pleated cover 26 is provided with a ring of adhesive 36 on its inner surface 28 for attachment to either the diaphragm 16 of stethoscope 10 (FIG. 1) or to the rim 62 of the bell portion of stethoscope 54 (FIG. 22). The adhesive ring 36 may extend completely or only partially around the outer circumferential edge of the cover.

When the pleated cover 26 of FIG. 20 is applied to the diaphragm 16, it is applied in a generally flat configuration as shown in solid lines in FIG. 21. However, when applied to bell rim 62, the cover is applied as shown in dashed lines in FIG. 21. This configuration is represented in FIG. 22 as a cup-shaped cover. To form a cup-shaped central portion from the planar pleated cover 26, all that is required is mild finger pressure applied to its center 34 to conform the cover to the walls of recess 50 in bell 52.

Figure 23:
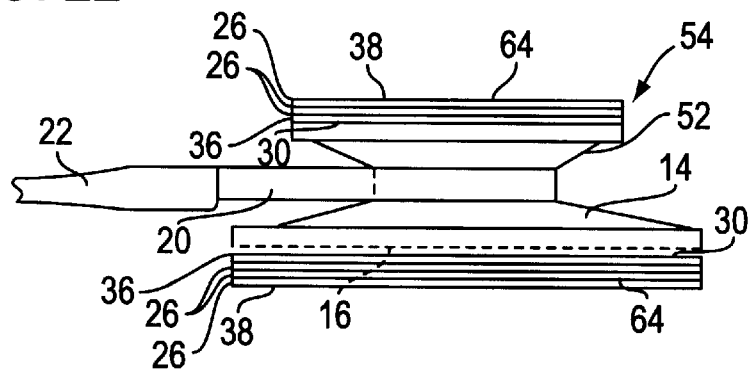
FIG. 23 is a side view of the stethoscope of FIG. 22 fitted with a stack of stethoscope covers in accordance with another embodiment of the invention.

Instead of removing and replacing a cover 26 on a stethoscope for use on each new patient, it is possible to provide a stack of covers 64 on the contact surfaces of the stethoscope, i.e. the bell 52 and/or the diaphragm 16 as shown in FIG. 23. In this embodiment, only the first cover 26 next to the diaphragm and bell is provided with an adhesive portion 30 for affixing each respective stack to the stethoscope 10.

The remaining covers 26 in each stack 64 may be held together by electrostatic attraction of the type commonly associated with plastic food wrapping sheets. Of course, adhesive 36 may be applied between adjacent layers if a positive bond is desired to positively maintain stack 64 as a unitary assembly.

In the various embodiments showing the stack of covers, it should be appreciated, that each of the covers could be formed with less adhesive than the previous cover in order to facilitate the operation. Furthermore, the pull tabs at the ends of the covers could be offset from each other, again to facilitate operation. It should also be appreciated that each of the covers could include antimicrobial or antiseptics. Such could be either included in the cover material, as for example through plastic injection molding, or the like, or could be included as part of the adhesive material.

There is currently also available a unique type of tape strip dispenser offered by 3M Corporation and is shown by way of example in any of their U.S. Pat. Nos. 5,401,547, 5,299, 712 and 5,086,946. All of that material is incorporated herein by reference. Such a dispenser could also be used for the present stack of covers. Of course, however, the covers would have to be appropriately modified with rough surface, and the like, as described in those patents.

There has been disclosed heretofore the best embodiment of the invention presently contemplated. However, it is to be understood that the various changes and modifications may be made thereto without departing from the spirit of the invention.

What is claimed:

1. A stack of stethoscope covers, comprising:
   a plurality of adjoining flexible sheets, each having an inner surface, an outer surface, a center, a peripheral edge and an adhesive provided on said inner surface defining an adhesive portion and a non adhesive portion, said non adhesive portion extending over said center and to said peripheral edge; and
   said adhesive portion of each one of said sheets attached to said outer surface of an adjoining one of said sheets.

2. The stack of claim 1, wherein said adhesive portion of each of said sheets is aligned over said non adhesive portion of said adjoining one of said sheets.

3. The stack of claim 1, wherein said adhesive portion comprises a segment-shaped portion.

4. The stack of claim 1, wherein said adhesive portion comprises a sector-shaped portion.

5. The stack of claim 1, wherein said sheets are stacked in an alternating zig-zag accordion configuration.

6. The stack of claim 1, wherein each one of said sheets comprises a pull tab.

7. The stack of claim 1, wherein said adhesive portion of each of said sheets is aligned over said adhesive portion of said adjoining one of said sheets.

8. The stack of claim 1, wherein each of said sheets is rotated in position with respect to each said adjoining one of said sheets so as to form a spiral pattern in said stack.

9. The stack of claim 1, wherein each of said sheets comprises an antimicrobial and/or antiseptic material.

10. A stack of stethoscope covers, comprising:

a plurality of adjoining flexible sheets, each having an inner surface adapted to be mounted to a stethoscope, an outer surface for contacting a patient, a center, a peripheral edge and an adhesive provided on said inner surface defining an adhesive portion and a non adhesive portion extending over said center and to said peripheral edge;

said adhesive portion of each one of said sheets attached directly to said outer surface of an adjoining underlying one of said sheets, said sheets being releasably adhesively interconnected up to a portion of each said peripheral edge.

11. The stack of claim 10, wherein said adhesive portion of each of said sheets is aligned over said non adhesive portion of said adjoining one of said sheets.

12. The stack of claim 10, wherein said adhesive portion comprises a segment-shaped portion.

13. The stack of claim 10, wherein said adhesive portion comprises a sector-shaped portion.

14. The stack of claim 10, wherein said sheets are stacked in an alternating zig-zag accordion configuration.

15. The stack of claim 10, wherein each one of said sheets comprises a pull tab.

16. The stack of claim 10, wherein said adhesive portion of each of said sheets is aligned over said adhesive portion of said adjoining one of said sheets.

17. The stack of claim 10, wherein each of said sheets is rotated in position with respect to each said adjoining one of said sheets so as to form a spiral pattern in said stack.

18. The stack of claim 10, wherein each of said sheets comprises an antimicrobial and/or antiseptic material.

19. The stack of claim 10, wherein said sheets are arranged in the manner of leaves in a book.

* * * * *